United States Patent [19]

Byers et al.

[11] Patent Number: 4,740,627
[45] Date of Patent: Apr. 26, 1988

[54] SYNTHESIS OF E,Z-11-TETRADECEN-1-AL

[75] Inventors: Jim D. Byers, Bartlesville; Charles A. Drake, Nowata, both of Okla.

[73] Assignee: Phillips Petroleum Company, Bartlesville, Okla.

[21] Appl. No.: 53,297

[22] Filed: May 21, 1987

[51] Int. Cl.$^4$ .................. C07C 41/06; C07C 45/29
[52] U.S. Cl. .................. 568/469.9; 568/471; 568/474; 568/485; 568/486
[58] Field of Search .................. 568/469.9, 471, 474, 568/485, 486

[56] References Cited

U.S. PATENT DOCUMENTS

| | | | |
|---|---|---|---|
| 3,917,711 | 11/1975 | Roelofs et al. | 260/601 R |
| 3,959,190 | 5/1976 | Weinshenker | 568/485 |
| 4,212,830 | 7/1980 | Weisner | 568/486 |
| 4,529,825 | 7/1985 | Yamamoto et al. | 568/903 |
| 4,540,826 | 9/1985 | Banasiak et al. | 568/420 |
| 4,560,792 | 12/1985 | Banasiak | 560/261 |
| 4,579,977 | 4/1986 | Drake | 568/490 |
| 4,609,498 | 9/1986 | Banasiak et al. | 260/410.9 R |

OTHER PUBLICATIONS

ApSimon, John, *The Total Synthesis of Natural Products*, vol. 4, p. 19.

"Insect Pheromones; I. Synthesis of Achiral Components of Insect Pheromones", Renzo Rossi, (1977), pp. 821–822.

Agis E. Kydonieus, *Insect Suppression with Controlled Release Pheromone Systems*, vol. II (1982), p. 178.

*Primary Examiner*—Werren B. Lone
*Attorney, Agent, or Firm*—Hal Brent Woodrow

[57] ABSTRACT

The present invention pertains to a process for making a E,Z-11-tetradecen-1-al containing from 80 to 83 mole percent of the E isomer and from 17 to 20 mole percent of the Z isomer which exhibits pheromone-like activity for the spruce bud worm (*choristoneura fumiferana*).

22 Claims, No Drawings

SYNTHESIS OF E,Z-11-TETRADECEN-1-AL

The present invention relates to a process for producing a E,Z-11-tetradecen-1-al possessing pheromone-like activity.

Pheromone is the name given to a wide variety of organic compounds which fulfill a quasi-hormonal, or more accurately, an intraspecies communication role. The female insect produces a minute amount of the pheromone which is detected by the male of the species and acids him in finding and mating with the female.

Sex pheromones have enormous potential in insect control, as they appear to be harmless to other forms of life and are relatively species specific. They may be used in a number of ways, e.g., in trapping of male insects and in confusion of male insects so that they fail to find the female, thus preventing mating and reproduction.

The pheromone for the spruce bud worm (*Choristoneura fumiferana*) is E,Z-11-tetradecen-1-al containing 96% of the E (trans) isomer and 4% of the Z (cis) isomer.

While synthetic routes for the preparation of E,Z-11-tetradecen-1-al have been disclosed in the prior art, these processes are not amendable to being carried economically on a large scale. All of these routes suffer from the disadvantage of requiring multiple reaction steps with consequent low overall product yield and consumption of large quantities of expensive reagents which do not contribute to the final product structure and the like.

Thus, it would be a valuable contribution to the art to develop a synthetic route for producing an E,Z-11-tetradecen-1-al possessing pheromone-like activity which is amendable to being carried out economically on a large scale.

It is thus an object of the present invention to produce an E,Z-11-tetradecen-1-al possessing pheromone-like activity which is amendable to being carried out economically on a large scale.

Other aspects and objects of this invention will become apparent hereinafter as the invention is more fully described.

In accordance with the present invention, it has been discovered that an E,Z-11-tetradecen-1-al possessing pheromone-like activity for the spruce bud worm, *Choristoneura fumiferana*, can be produced by:

(1) isomerizing an 11-tetradecen-1-ol with nitrogen dioxide, thereby producing an E,Z-11-tetradecen-1-ol having a stereochemical orientation of about 80-83 mole percent E (trans) and about 20-17 mole percent Z (cis); and thereafter (2) oxidizing the resulting isomerized E,Z-11-tetradecen-1-ol into E,Z-11-tetradecen-1-al having a stereochemical orientation of about 80-83 mole percent E (trans) and about 20-17 mole percent Z (cis).

While this synthetic route produces an E,Z-11-tetradecen-1-al having a stereochemical orientation differing from that of the spruce bud worm's natural pheromone; the E,Z-11-tetradecen-1-al produced in accordance with the present invention still possesses pheromone-like activity for the spruce bud worm.

As used in this application, the term pheromone-like activity refers to the ability of the E,Z-11-tetradecen-1-al produced in accordance with the present invention to mimic the biological properties of the E,Z-11-tetradecen-1-al naturally secreted by the female spruce bud worm.

The starting material in the synthesis of the present invention is 11-tetradecen-1-ol. The relative concentrations of the Z and E isomers present therein is not critical to the practice of the present invention. Suitable Z to E ratios in the 11-tetradecen-1-ol range from 100:0 to 0:100.

It is currently preferred, however, that the 11-tetradecen-1-ol utilized contain about 50 mole percent of the Z isomer and about 50 mole percent of the E isomer.

The manner in which the E,Z-11-tetradecen-1-ol is prepared is not critical to the practice of the present invention. This compound is available commercially from several suppliers. Any of the commercially available compounds are suitable for practice in the present invention.

However, in one presently preferred embodiment of this invention an E,Z-11-tetradecen-1-ol is prepared in the following 3-step synthesis:

(a) disproportionating cyclooctene and 1-butene in the presence of a suitable disproportionation catalyst under conditions suitable to produce 1,9-dodecadiene;

(b) metallating the 1,9-dodecadiene obtained in step (a) with a metallating agent under conditions suitable to form a 1-metallo-9-dodecene; and (c) reacting the 1-metallo-9-dodecene obtained in step (b) with ethylene oxide under conditions suitable to form E,Z-11-tetradecen-1-ol.

The disproportionation of cyclooctene and 1-butene can be carried out in a variety of ways as recognized by those of skill in the art. Thus, any suitable ratio of cyclooctene/1-butene can be employed in the presence of a wide variety of disproportionation catalysts. For the most efficient utilization of the olefinic reactants, a molar ratio of about 1:1 is preferred, although good conversions are obtained with cyclooctene/1-butene ratios ranging from about 5:1 to about 1:5.

A wide variety of heterogeneous and homogeneous disproportionation catalysts are known in the art and are capable of promoting the disproportionation of cyclooctene and 1-butene to produce 1,9-dodecadiene. Our invention is not limited to the use of a specific disproportionation catalyst, but any catalyst suitable for the disproportionation of cyclooctene and 1-butene can be utilized.

Suitable catalysts for use in the disproportionation reaction of the present invention include:

(1) silica or thoria promoted by an oxide or compound convertible to an oxide by calcination, or sulfide of tungsten or molybdenum; or by an oxide or compound convertible to an oxide by calcination of rhenium or tellurium;

(2) alumina promoted with an oxide or compound convertible to an oxide by calcination of molybdenum, tungsten, or rhenium; a sulfide of tungsten or molybdenum; or an alkali metal salt, ammonium salt, alkaline earth metal salt, or bismuth salt of phosphomolybdic acid;

(3) one or more of the group aluminum phosphate, zirconium phosphate, calcium phosphate, magnesium phosphate, or titanium phosphate promoted by one or more of a sulfide of molybdenum or tungsten, or an oxide or compound convertible to an oxide by calcination of molybdenum, tungsten or rhenium or magnesium tungstate or beryllium phosphotungstate;

(4) silica, alumina, aluminum phosphate, zirconium phosphate, calcium phosphate, magnesium phosphate, or titanium phosphate promoted by a hexacarbonyl of molybdenum or tungsten; and (5) (a) molybdenum oxide or tungsten oxide associated with suitable support material and (b) at least one organoaluminum compound, optionally, treated with nitric oxide or nitrosyl halides.

These catalysts as well as their methods of activation are known in the art. The conditions under which a disproportionation reaction would be carried out with these catalysts is also known in the art. U.S. Pat. No. 4,609,498 issued to Banasiak et al which is currently assigned to Phillips Petroleum Company, discloses these catalysts, their methods of preparation, and suitable reaction conditions for carrying out disproportionation reactions with these catalysts. This reference is hereby incorporated by reference.

The presently preferred disproportionation catalyst is a silica-supported molybdenum catalyst. The anion associated with the molybdenum is not critical, but is preferably an oxide or sulfide. The catalyst can be activated by heating it in an inert atmosphere.

If desired, the molybdenum can be washed with a base such as potassium hydroxide, sodium hydroxide, or ammonium hydroxide prior to or after it has been contacted with the silica.

The manner in which the disproportionation reaction is carried out is not critical to the practice of the present invention. Generally, the 1-butene and the cyclooctene will be contacted with a silica-supported molybdenum catalyst in the presence of heat.

Generally, the disproportionation reaction should be carried out at a temperature range of from 40° C. to 300° C., and more preferably from 120° C. to 220° C. The pressure in the reaction environment should generally be in the broad range of 50 to 1500 psig and more preferably from 100 to 400 psig.

If the reaction is conducted in a batch wise manner, then it is preferred that the reaction be carried out for a period of time ranging from 0.5 hours to 18 hours.

If the reaction is carried out in a continuous reactor, then it is preferred that the reaction have a weight hour velocity of 0.5 to 70 grams/grams/hour, more preferably from 1 to 40 grams/grams/hour.

The next step in the preferred synthesis of the starting material, E,Z-11-tetradecen-1-ol; is to metallate the 1,9-dodecadiene obtained in the disproportionation reaction of step (a) in order to form a 1-metallo-9-dodecene.

The metallation of 1,9-dodecadiene to form a 1-metallo-9-dodecene can be carried out employing a variety of metallating agents. Any metallating agent capable of selective reaction with the terminal double bond of the diene starting material is suitable. Examples of suitable metallating agents include organoboranes, organoaluminum compounds, organomagnesium compounds, and the like. Organomagnesium compounds are currently preferred.

Organoboranes contemplated to be within the scope of the present invention can be described as "hindered" organoborane compounds and can be represented by the following formula:

$$R_2BH$$

wherein each R is independently selected from the group consisting of $C_2$ to $C_{10}$ carbon radicals, wherein at least one R group is a secondary or tertiary alkyl group and each R group can be connected to the other as part of a ring structure. Exemplary compounds which satisfy the above formula include disiamylborane (i.e., bis-(3-methyl-2-butyl)borane), 9-boradicyclo[3.3.1-]nonane (9-BBN), dithexylborane, thexylcyclopentylborane, thexylcyclohexylborane, and the like.

The hydroboration reaction is generally carried out in the presence of a suitable solvent such as, for example, tetrahydrofuran (THF). A roughly equimolar mixture of diene and organoborane reagent are combined. Preferably, a slight excess of diene is employed to minimize the likelihood of hydroboration occurring on the internal double bonds of the starting material diene. Typically, the hydroboration reaction should be excluded from the reaction mixture. Reaction conditions employed are broadly 0°-100° C. for a few minutes up to several hours. Preferably, the hydroboration is carried out at about 20°-80° C. for 15 minutes up to about 2 hours. Reaction is generally carried out at about atmospheric pressure, although higher and lower pressures are acceptable.

Organoaluminum compounds contemplated to be within the scope of the present invention can be described by reference to the formula:

$$R_2AlH$$

wherein R is as defined above for the organoboranes. Examples of suitable organoaluminum compounds include diisobutylaluminum hydride, diisopropylaluminum hydride and the like.

Metallation with organoaluminum compounds is generally carried out at atmospheric pressure, although higher and lower pressures are operable. Preferably, atmospheric pressure or slightly reduced pressures will be employed since pressures in excess of atmospheric will tend to retard the reaction rate. Reaction temperatures of about 20° to about 100° C. for at least one minute up to about 24 hours are suitable. Preferably, reaction temperature will be maintained between about 20° C. and 60° C. for about 15 minutes to about 6 hours.

Organomagnesium compounds contemplated to be within the scope of the present invention can be described by reference to the following formulae:

$$R'MgX, \text{ and}$$

$$R'_2Mg$$

wherein R' is selected from the group consisting of a $C_3$ to $C_{10}$ carbon radical, more preferably a $C_3$ to $C_6$ carbon radical; which has at least one β-hydrogen and X is selected from the group consisting of Cl, Br or I. Exemplary compounds which satisfy the above formulae include various Grignard reagents, such as, for example, butylmagnesium bromide, isopropylmagnesium bromide, and the like. Additional examples include dialkyl magnesium compounds such as for example diethylmagnesium, diisopropylmagnesium and the like.

The most preferred magnesium compounds can be selected from the group consisting of butylmagnesium bromide, butylmagnesium chloride, or butylmagnesium iodide, propylmagnesium bromide, propylmagnesium chloride, isopropylmagnesium bromide, isopropylmagnesium chloride, isopropylmagnesium iodide, propylmagnesium iodide, pentylmagnesium bromide, pentylmagnesium iodide, pentylmagnesium chloride, hexylmagnesium bromide, hexylmagnesium chloride and hexylmagnesium iodide.

Metallation with organomagnesium compounds is generally carried out in the presence of at least one transition metal activating agent. Suitable transition metal activating agents include nickel, titanium, vanadium and zirconium compounds. Exemplary titanium activating agents include a titanocene dichloride such as, for example, dicyclopentadiene titanium dichloride or alternatively, titanium tetrachloride.

The molar ratio of organomagnesium compound to diene should be at least about 1:1 with the presence of a small excess of the organomagnesium compound acceptable, i.e., up to about a 1.5 to 1 molar ratio. The molar ratio of diene to transition metal reagent is generally in the range of about 1–500:1 and preferably about 50–100:1.

Metallation with organomagnesium compounds is generally carried out at atmospheric pressure, although higher and lower pressures are operable. Preferably, atmospheric pressure or slightly reduced pressures will be employed since pressures in excess of atmospheric will tend to retard the reaction rate. Reaction temperatures of about 20° to about 100° C. for at least one minute up to about 24 hours are suitable. Preferably, reaction temperature will be maintained between about 20° and 60° C. for about 15 minutes to about 6 hours.

The final step in the preferred synthesis of the starting material, E,Z-11-tetradecen-1-ol is to react the 1-metallo-9-dodecene obtained in step (b) with ethylene oxide in order to produce E,Z-11-tetradecen-1-ol.

The exact manner in which the ethylene oxide is reacted with the 1-metallo-9-dodecene is not critical to the practice of the present invention, provided that the ethylene oxide displaces the 1-metallo function and thereby forms a new carbon-carbon bond with the 1 carbon of the 1-metallo-9-dodecene.

Generally, it is preferred that there be a slight excess of ethylene oxide present relative to the 1-metallo-9-dodecene. However, suitable molar ratios of 1-metallo-9-dodecene to ethylene oxide range from 1:1 to 1:5.

It is also preferred that the reaction between ethylene oxide and the 1-metallo-9-dodecene be carried out in the presence of a copper (I) catalyst. Suitable copper (I) catalysts can be selected from the group consisting of copper (I) iodide, copper (I) bromide, and copper (I) chloride.

The copper should be present in the range of about 1 to 20 mole percent based on the moles of organometallic species employed. More preferably, the copper is present in the quantity of about 2 to 10 mole percent.

It is also preferred that the reaction be conducted in a tetrahydrofuran solvent.

Typically, the reaction is carried out at a temperature range of from −20° C. to 80° C. for 0.5 to 10 hours. Preferably, the reaction is carried out at about −10° C. to 20° C. for 1 to 2 hours.

It is also preferred that the reaction product be washed with a dilute acid, such as hydrochloric acid.

Regardless of whether the 11-tetradecen-1-ol is produced by the above 3-step synthesis or whether it is a commercially available compound produced in another manner; an E,Z-11-tetradecen-1-ol possessing pheromone-like activity for the spruce bud worm can be produced by:

(1) isomerizing an 11-tetradecen-1-ol with nitrogen dioxide, thereby producing an E,Z-11-tetradecen-1-ol having a stereochemical orientation of about 80-83 mole percent E (trans) and 20-17 mole percent Z (cis); and (2) oxidizing the resulting isomerized E,Z-11-tetradecen-1-ol into E,Z-11-tetradecen-1-al.

The stereochemical orientation of the 11-tetradecen-1-ol utilized as the starting material is not critical to the practice of the present invention. The 11-tetradecen-1-ol can be the pure Z isomer, pure E isomer or a mixture of the Z and E isomers. Suitable molar ratios of the Z to E isomer range from 0:100 to 100:0.

The 11-tetradecen-1-ol is isomerized into a mixture of E and Z 11-tetradecen-1-ol containing from 80-83 mole percent of the E isomer and 17 to 20 mole percent of the Z isomer by contacting the 11-tetradecen-1-ol with nitrogen dioxide.

The quantity of nitrogen dioxide used in isomerizing the 11-tetradecen-1-ol is not critical to the practice of the present invention. It is currently preferred, however, that the nitrogen dioxide be present in the quantity of 1 to 10 mole percent, and more preferably 2 to 3 mole percent based on the quantity of 11-tetradecen-1-ol present in the reaction zone.

Typically, the nitrogen dioxide will be contacted with the Z and E-11,tetradecen-1-ol for a period of time ranging from 2 to 4 hours, at a temperature of from 20° C. to 50° C. If desired, an organic solvent such as hexane can be present in the reaction zone.

After the desired stereochemistry of the Z and E 11-tetradecen-1-ol is achieved, the 1-position alcohol of the Z and E 11-tetradecen-1-ol is oxidized into an aldehyde with a suitable oxidizing agent under suitable conditions.

One group of suitable oxidizing agents are those selected from the group consisting of pyridinium chlorochromate and pyridinium dichromate. Another suitable oxidizing agent is DMSO (dimethyl sulfoxide).

If the oxidation is conducted with either pyridinium chlorochromate or pyridinium dichromate, then it is preferred that the oxidizing agent be present in a molar excess relative to the E,Z-11-tetradecen-1-ol. Suitable ratios of oxidizing agents to E,Z-11-tetradecen-1-ol will be in the range of from 1:1 to 5:1, more preferably 1.5:1 to 3:1.

Typical reaction conditions with the pyridinium oxidizing agents will include a reaction temperature in the range of from 20° C. to 50° C., for a period of time ranging from 15 minutes to 3 hours.

It is also preferred that the reaction be conducted in an organic halide solvent, such as methylene chloride.

The E,Z-11-tetradecen-1-al can then be separated from the reaction medium by an extraction step utilizing an oxygenated organic solvent such as an ether.

The E,Z-11-tetradecen-1-al can then be separated from the oxygenated organic phase by wiped film distillation at a temperature of 160° C. to 167° C. and at a pressure of 0.2 mm Hg.

If DMSO is utilized as the oxidizing agent, then it is preferred that the oxidation be conducted in the presence of an activator; suitable activators can be selected from the group consisting of oxalyl chloride, trifluoroacetic anhydride and acetic anhydride, and thionyl chloride.

It is also preferred that the activator be present in a molar excess relative to the E,Z-11-trecadecen-1-ol. Suitable ratios of activator to E,Z-11-tetradecen-1-ol will be in the range of from 1:1 to 5:1, more preferably 1.5:1 to 3:1.

It is also preferred that the oxidation with DMSO be conducted in the presence of an organic amine base. Suitable organic amine bases can be selected from the group consisting of triethylamine, trimethylamine, tripropylamine, tributylamine, tripentylamine, trihexylamine and pyridine.

It is currently preferred that the oxidizing agent, DMSO, be present in the reaction zone in a molar excess relative to the E,Z-11-tetradecen-1-ol. Suitable ratios of DMSO to E,Z-11-tetradecen-1-ol will be in the range of from 1:1 to 5:1, more preferably 1.5:1 to 3:1.

It is also preferred that the organic amine base be present in the reaction zone in a molar excess relative to the E,Z-11-tetradecen-1-ol. Suitable ratios of organic amine base to E,Z-11-tetradecen-1-ol will be in the range of from 1:1 to 5:1, more preferably 1.5:1 to 3:1.

Typically, the reaction will be conducted at a temperature range of from −60° C. to 0° C. for a period of time ranging from 15 minutes to 6 hours.

It is also preferred that the reaction be conducted in an organic solvent, such as ether, methylene chloride or tetrahydrofuran.

The E,Z-11-tetradecen-1-ol can be separated from the reaction zone by adding water to the reaction zone and extracting the E,Z-11-tetraceden-1-ol. The by-products will be concentrated in the water phase and the E,Z-11-tetraceden-1-ol will be concentrated in the organic phase.

The E,Z-11-tetradecen-1-ol can then be separated from the organic phase by wiped film distillation at a temperature of 160° C. to 167° C. and at a pressure of 0.2 mm Hg.

A further understanding of the present invention and its advantages will be provided by reference to the following examples.

EXAMPLE I

The purpose of this example is to demonstrate a preferred manner for carrying out the disproportionation reaction between cyclooctene and 1-butene, thereby forming 1,9-dodecadiene.

A. Disproportionation Catalyst Preparation

Disproportionation catalysts were prepared by pouring an aqueous solution of a catalyst precursor over a quantity of catalyst support contained in a beaker fastened to a rotating table. The solution was added at a rate that permitted good absorption of the solution by the silica support.

The catalyst employed for the following run was prepared by pouring 26 mls of the solution containing 2.6 grams of ammonium molybdate (13 mmol) and 0.5 grams of potassium hydroxide (0.9 mmol) over 20 grams of a high surface area silica support. Once all the support-treating solution had been added to the support, the treated support was oven dried at 350° C. for about 3 hours.

5 grams of the catalyst was then loaded into a vertical pipe reactor (½" diameter by about 20 inches in length). The catalyst was then air oxidized for about 6 hours at 450° C., then CO treated at 450° and 125 psig for about 1 hour, and finally cooled to the desired reaction temperature of about 140° C.

B. Disproportionation Reaction

A mixture of 990 grams of cyclooctene (9 moles) and 1340 grams of 1-butene (24 moles) was passed through a guard bed of about ⅓ 3A molecular sieves, ⅓ - 13 X molecular sieves and ⅓ γ-alumina. The pretreated feed was then introduced at the rate of about 4 mls per minute to the catalyst bed prepared as described above, which was maintained at a reaction temperature of about 140° C. and a reaction pressure of about 200 psig. The yield of the desired 1,9-dodecadiene was about 12 percent, as calculated by gas-liquid chromatographic analysis.

Approximately 60 percent of the reaction product was unreacted 1-butene and unreacted cyclooctene. These unreacted reagents can be recycled and utilized in subsequent reactions. This ability to recycle unreacted reagents is one of the advantages of the present invention that makes it suitable for economical large scale industrial synthesis.

EXAMPLE II

The purpose of this example is to:
(a) demonstrate a method for producing a 1-metallo-9-dodecene from 1,9-dodecadiene; and
(b) a process for making E,Z-11-tetradecene-1-ol from the 1-metallo 9-dodecene produced in step (a).

1000 grams of 1,9 dodecadiene was prepared in the manner disclosed in Example I.

A 12 liter, 3 necked flask equipped with a mechanical stirrer, addition funnel and reflux condenser was purged with argon.

The 12 liter, 3 necked flask was then charged with the 1000 grams (6 moles) of 1,9 dodecadiene, (6 moles) of butyl magnesium chloride which was dissolved in two liters of diethyl ether and 11 grams, (0.044 moles) of titanocene dichloride.

The reactants were then heated to 60° C. and maintained at that temperature for about 3 hours. The reactants were mechanically stirred during this heating period.

After 3 hours the reactants were then cooled to 0° C.

After the reactants had reached 0° C., 2 liters of tetrahydrofuran and 3.5 grams of cuprous bromide were added to the reaction vessel.

The reaction mixture was maintained at a temperature between about 0° C. and −15° C. while 300 grams of ethylene oxide was slowly added to the reaction zone over about a 2½ hour period. For convenience, the reaction mixture was then stirred overnight at 25° C.

The E,Z-11-tetradecen-1-ol was separated from the reaction mixture in the following manner: 3000 mls of a 3 molar hydrochloric acid solution and 3000 mls of hexane were added to the reaction mixture. The E,Z-11-tetraceden-1-ol was concentrated in the organic phase. The organic phase was then separated from the aqueous phase which contained the by-products of the reaction.

The organic phase was then washed with approximately 2 liters of a sodium bicarbonate solution and the organic phase was again separated. This organic solution was then partially concentrated with a rotary evaporator.

The E,Z-11-tetradecen-1-ol was then recovered from this concentrated solution by distillation under vacuum at a temperature of approximately 110° C. and 0.2 mls of mercury.

GLC analysis indicated a 30 percent yield of E,Z-11-tetradecen-1-ol based on the diene starting material.

It is important to point out that 2 different synthetic steps occurred during the reaction sequence set out in this example. Heating the 1,9-dodecadiene in the presence of butyl magnesium chloride and titanicene dichloride produced a 1-metallo-9-dodecene.

This 1-metallo-9-dodecene was then transformed into E,Z-11-tetradecen-1-ol by contacting the metallo compound with cuprous bromide and ethylene oxide.

Thus, in addition to a high yield, the present invention also has the advantage of not requiring a separation and recovery after every step in the synthesis.

EXAMPLE III

The purpose of this example is to demonstrate a method for isomerizing a mixture of Z and E-11-tetradecen-1-ol which contains approximately 50 mole percent of the Z isomer and approximately 50 mole percent of the E isomer into a mixture of Z and E-11-tetradecen-1-ol containing about 83 percent of the E (trans) isomer and about 17 mole percent of the Z (cis) isomer.

A 300 cc stainless steel autoclave was charged with 150 grams of E,Z-11-tetradecen-1-ol containing approximately 50 mole percent of the Z isomer and approximately 50 mole percent of the E isomer which had been prepared in the manner disclosed in Example I and II. This autoclave was also charged with approximately 5 grams of nitrogen dioxide. 150 mls of hexane were also added.

The reaction mixture was heated to 35° C. and maintained at that temperature for 6 hours. The reaction mixture was stirred during the reaction period.

After the reaction was completed, the Z and E 11-tetradecen-1-ol containing 83 mole percent of the E isomer and 17 mole percent of the Z isomer was separated from the reaction mixture in the following manner. 500 mls of a saturated sodium bicarbonate solution was added to the reaction mixture. The E,Z-11-tetradecen-1-ol was concentrated in the organic phase and the nitrogen dioxide was concentrated in the aqueous phase. The phases were separated and the organic phase containing the E,Z-11-tetradecen-1-ol was dried with magnesium sulfate. The organic phase was then filtered to remove the magnesium sulfate and subjected to rotary concentration.

Analysis of the product by gas chromatography showed Z and E 11-tetradecen-1-ol had been isomerized into a mixture of Z and E 11-tetradecen-1-ol containing about 83 mole percent of the E isomer and about 17 mole percent of the Z isomer.

Thus, this example demonstrates the ease with which the desired stereochemistry can be achieved by the present invention. It also demonstrates that it is not necessary to recover the E,Z-11-tetradecen-1-ol prior to the oxidation.

EXAMPLE IV

The purpose of this example is to demonstrate one of the several methods which are suitable for oxidizing the E,Z-11-tetradecen-1-ol into E,Z-11-tetradecen-1-al.

100 grams (0.47 moles) of E,Z-11-tetradecen-1-ol had been prepared in the manner disclosed in Examples I–III.

A 2 liter, 3-necked flask equipped with a mechanical stirrer, addition funnel, and reflux condenser was charged with 152 grams (0.71 mole) of pyridinium chlorochromate and 500 mls of methylene chloride. The 100 grams of E,Z-11-tetradecen-1-ol and an additional 100 mls of methylene chloride were placed in the addition funnel of the 3-necked flask.

The E,Z-11-tetradecen-1-ol was dripped into the reaction zone over about a 20 minute period.

The reaction mixture was then stirred for about 1 hour at room temperature. The E,Z-11-tetradecen-1-al was recovered from the reaction mixture in the following manner.

The reaction mixture was washed three times with about 250 mls of ether. After each washing, the liquid was decanted off and saved.

The decanted liquid was then collected together and concentrated on a rotary evaporator. After concentration, the liquid was then wiped-film distilled at a surface temperature of about 167° C. and about 0.2 mm of mercury.

The yield of E,Z-11-tetradecen-1-al was about 75 percent based upon the distillation yield.

Thus, the above example demonstrates that pyridinium chlorochromate will oxidize the E,Z-11-tetradecen-1-ol into E,Z-11-tetradecen-1-al in yields high enough to be conducted economically on a large scale industrial synthesis.

EXAMPLE V

The purpose of this example is to demonstrate that the oxidizing agent, DMSO, will also oxidize E,Z-11-tetradecen-1-ol into E,Z-11-tetradecen-1-al at yields high enough to support an economically viable large scale industrial synthesis.

2.12 grams (0.01 moles) of E,Z-11-tetradecen-1-ol was prepared in the manner described in examples I–III.

A 300 ml 3-necked flask equipped with a mechanical stirrer, addition funnel and reflux condenser was charged with 0.02 moles of oxalyl chloride, and 25 mls of methylene chloride. The flask was then cooled to −15° C.

The addition funnel of the flask was charged with 0.04 moles of DMSO and 5 mls of methylene chloride. DMSO and methylene chloride were then dripped into the reaction mixture over about a 10 minute period while maintaining the reaction mixture at a temperature of about −15° C.

The addition funnel was then charged with 2.12 grams of E,Z-11-tetradecen-1-ol and 5 mls of methylene chloride. The E,Z-11-tetradecen-1-ol and the methylene chloride were then dripped in over a 5 minute period, while maintaining the reaction mixture at a temperature of about −15° C.

The reaction mixture was then stirred for 15 minutes and 0.04 moles of triethyl amine were added to the reaction mixture.

The reaction mixture was stirred for an additional 5 minutes at −15° C.

At that point, the reaction mixture was allowed to warm to room temperature and the E,Z-11-tetradecen-1-al was recovered.

The E,Z-11-tetradecen-1-al was recovered in the following method: 200 mls of H$_2$O and 200 mls of methylene chloride were added to the reaction mixture. The E,Z-11-tetradecen-1-al was concentrated in the organic phase. These phases were separated and the organic phase was concentrated on a rotary evaporator.

After concentration, the E,Z-11-tetradecen-1-al was recovered by wiped-film distillation conducted at a surface temperature of about 150° C. and about 0.2 mm of Hg.

The yield of E,Z-11-tetradecen-1-al was 90 percent based upon the distilled yield.

Thus, this example demonstrates that when DMSO is utilized as an oxidizing agent, E,Z-11-tetradecen-1-ol can be converted into E,Z-11-tetradecen-1-al at yields high enough to permit the large scale industrial synthesis of the desired pheromone.

EXAMPLE VIII

The purpose of this example is to demonstrate that other activators besides oxalyl chloride, can be used to aid the oxidation of E,Z-11-tetradecen-1-ol by DMSO.

2.12 grams (0.01 moles) of E,Z-11-tetradecen-1-ol was prepared in the manner described in Examples I–III.

A 300 ml 3-necked flask equipped with a mechanical stirrer, addition funnel and reflux condenser was charged with 0.02 moles of thionyl chloride, and 25 mls of ether. The flask was then cooled to $-15°$ C.

The addition funnel of the flask was charged with 0.04 moles of DMSO and 5 mls of ether. DMSO and ether were then dripped into the reaction mixture over about a 10 minute period while maintaining the reaction mixture at a temperature of about $-15°$ C.

The addition funnel was then charged with 2.12 grams of E,Z-11-tetradecen-1-ol and 5 mls of ether. The E,Z-11-tetradecen-1-ol and the ether were then dripped in over a 5 minute period, while maintaining the reaction mixture at a temperature of about $-15°$ C.

The reaction mixture was then stirred for 15 minutes and 0.04 moles of triethylamine were added to the reaction mixture.

The reaction mixture was stirred for an additional 5 minutes at $-15°$ C.

At that point, the reaction mixture was allowed to warm to room temperature and the E,Z-11-tetradecen-1-al was recovered.

The E,Z-11-tetradecen-1-al was recovered in the following method: 200 mls of H$_2$O and 200 mls of ether were added to the reaction mixture. The E,Z-11-tetradecen-1-al was concentrated in the organic phase. These phases were separated and the organic phase was concentrated on a rotary evaporator.

After concentration, the E,Z-11-tetradecen-1-al was recovered by wiped-film distillation conducted at a surface temperature of about 150° C. and about 0.2 mm of Hg.

The yield of E,Z-11-tetradecen-1-al was 70 percent based upon the distilled yield.

Thus this example demonstrates that DMSO will successfully oxidize E,Z-11-tetradecen-1-ol into E,Z-11-tetradecen-1-al under a variety of reaction conditions.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of the patent protection desired and sought.

That which is claimed is:

1. A process for producing an E,Z-11-tetradecen-1-al comprising:
   (a) contacting an 11-tetradecen-1-ol with nitrogen dioxide under isomerization conditions thereby forming an E,Z-11-tetradecen-1-ol containing from 80 to 83 mole percent of the E isomer and 17 to 20 mole percent of the Z isomer thereafter;
   (b) oxidizing the resulting isomerized E,Z-11-tetradecen-1-ol with an oxidizing agent selected from the group consisting of pyridinium chlorochromate, pyridinium dichromate and dimethyl sulfoxide under oxidizing conditions.

2. The process of claim 1, wherein said nitrogen dioxide is present in the quantity of from 1 to 10 mole percent.

3. The process of claim 2, wherein said contact with nitrogen dioxide is conducted at a temperature of from 20° C. to 50° C. in the presence of an inert organic solvent.

4. The process of claim 1, wherein the molar ratio of said oxidizing agent to said E,Z-11-tetradecen-1-ol is in the range of from 1:1 to 5:1.

5. The process of claim 4, wherein said oxidation with said pyridinium dichromate and said pyridinium chlorochromate is conducted at a temperature range of from 20° C. to 50° C. in the presence of an inert organic solvent.

6. The process of claim 4, wherein said oxidation with said dimethyl sulfoxide is conducted in the presence of an activator selected from the group consisting of oxalyl chloride, trifluroacetic anhydride, acetic anhydride and thionyl chloride.

7. The process of claim 6, wherein the molar ratio of activator to said E,Z-11-tetradecen-1-ol is in the range of 1:1 to 5:1.

8. The process of claim 6, wherein said oxidation with said dimethyl sulfoxide is conducted in the presence of at least one organic amine base selected from the group consisting of trimethylamine, triethylamine, tripropylamine, tributylamine, tripentylamine, trihexylamine, and pyridine.

9. The process of claim 8, wherein the molar ratio of said organic amine base to said E,Z-11-tetradecen-1-ol is in the range of from 1:1 to 5:1.

10. The process of claim 8, wherein said oxidation with said DMSO is conducted at a temperature range of from $-60°$ C. to 0° C., in the presence of an inert organic solvent.

11. The process of claim 1, wherein said E,Z-11-tetradecen-1-ol is produced by a process which comprises:
   (a) disproportionating cyclooctene and 1-butene in the presence of a disproportionation catalyst under disproportionating conditions suitable to form 1,9-dodecadiene;
   (b) metallating the 1,9-dodecadiene of step (a) with a metallating agent under conditions suitable to form a 1-metallo-9-dodecene; and
   (c) reacting the 1-metallo-9-dodecene of step (b) with ethylene oxide under conditions suitable to form E,Z-11-tetradecen-1-ol.

12. The process of claim 1, wherein said disproportionation catalyst is selected from the group consisting of
   (a) silica or thoria promoted by an oxide or compound convertible to an oxide by calcination, or sulfide of tungsten or molybdenum; or by an oxide or compound convertible to an oxide by calcination of rhenium or tellurium;
   (b) alumina promoted with an oxide or compound convertible to an oxide by calcination of molybdenum, tungsten, or rhenium; a sulfide of tungsten or molybdenum; or an alkali metal salt, ammonium salt, alkaline earth metal salt, or bismuth salt of phosphomolybdic acid;
   (c) one or more of the group aluminum phosphate, zirconium phosphate, calcium phosphate, magnesium phosphate, or titanium phosphate promoted by one or more of a sulfide of molybdenum or tungsten, or an oxide or compound convertible to an oxide by calcination of molybdenum, tungsten or rhenium or magnesium tungstate or beryllium phosphotungstate;
(d) silica, alumina, aluminum phosphate, zirconium phosphate, calcium phosphate, magnesium phosphate, or titanium phosphate promoted by a hexacarbonyl of molybdenum or tungsten; and
(e) molybdenum oxide or tungsten oxide associated with suitable support material and at least one organoaluminum compound, optionally, treated with nitric oxide or nitrosyl halides.

13. The process of claim 12, wherein said catalyst is molybdenum oxide on a silica support.

14. The process of claim 13, wherein said molybdenum is treated with a base selected from the group consisting of KOH, NaOH, and $NH_4+OH$.

15. The process of claim 11 wherein said metallation is conducted in the presence of a metallating agent selected from the group consisting of:
(a) organoboranes of the formula $R_2BH$, wherein each R is independently selected from the group consisting of $C_1$–$C_{10}$ carbon radicals, wherein at least one R group is a secondary or tertiary alkyl group, optionally each R group can be connected to the other as part of a ring structure.
(b) organoaluminum compounds of the formula $R_2AlH$, wherein R is defined as above,
(c) organomagnesium compounds of the formula $R_2Mg$ wherein R is selected from the group consisting of a $C_3$–$C_{10}$ carbon radical and wherein each R group has at least one B-hydrogen; and
(d) organomagnesium compounds of the formula RMgX, wherein R is selected from the group consisting of a $C_3$–$C_{10}$ carbon radical; wherein each R group has at least one B hydrogen and X is selected from the group consisting of Cl, Br, and I.

16. The process of claim 15, wherein said metallation with an organomagnesium compound is conducted in the presence of at least one transition metal selected from the group consisting of nickel, titanium, vanadium and zirconium compounds.

17. The process of claim 16, wherein said transition metal activating agent is titanocene dichloride.

18. The process of claim 15, wherein the molar ratio of said metallating agent to said 1,9-dodecadiene is in the range of 1:1 to 1:5.

19. The process of claim 16 wherein the molar ratio of said transition metal activating agent to said 1,9-dodecadiene is in the range of from 1:500 to 1:1.

20. The process of claim 11 wherein said 1-metallo-9-dodecene is contacted with said ethylene oxide in the presence of at least one promoter selected from the group consisting of cuprous chloride, cuprous bromide, and cuprous iodide.

21. The process of claim 20 wherein said promoter is present in the range of from 1 to 20 mole percent based upon the moles of 1-metallo-9-dodecene present.

22. The process of claim 17, wherein
(a) said cyclooctene and said 1-butene are disproportionated in the presence of a molybdenum oxide catalyst;
(b) said 1,9-dodecadiene is metallated by butylmagnesium chloride and titanocene dichloride; and
(c) said 1-metallo-9-dodecene is contacted with said ethylene oxide in the presence of cuprous bromide.

* * * * *